United States Patent [19]

Sashin et al.

[11] Patent Number: 4,692,937
[45] Date of Patent: Sep. 8, 1987

[54] RADIOGRAPHY APPARATUS AND METHOD

[75] Inventors: Donald Sashin, Pittsburgh, Pa.; Ernest J. Sternglass, Bloomington, Ind.

[73] Assignee: University of Pittsburgh, Pittsburgh, Pa.

[21] Appl. No.: 606,057

[22] Filed: May 2, 1984

[51] Int. Cl.⁴ .................. A61B 6/00; G03B 42/02; H05G 1/60
[52] U.S. Cl. .................... 378/062; 378/99; 378/146
[58] Field of Search .............. 378/57, 146, 99, 62; 250/356.1; 73/861.05; 358/111

[56] References Cited

U.S. PATENT DOCUMENTS

| 3,395,283 | 7/1968 | Sefton et al. | 250/561 |
| 3,767,931 | 10/1973 | Williams | 250/511 |
| 3,829,701 | 8/1974 | Hura | 250/511 |
| 3,866,047 | 2/1975 | Hounsfield | 250/360 |
| 3,934,151 | 1/1976 | Stowe et al. | 250/505 |
| 3,947,689 | 3/1976 | Wagner | 250/512 |
| 3,973,127 | 8/1976 | Matsuda et al. | 250/445.7 |
| 4,010,371 | 3/1977 | Lemay | 250/366 |
| 4,029,964 | 6/1977 | Ashe | 250/368 |
| 4,179,100 | 12/1979 | Sashin et al. | 378/99 |
| 4,228,353 | 10/1980 | Johnson | 250/356.1 |
| 4,426,721 | 1/1984 | Wang | 378/99 |
| 4,484,340 | 11/1984 | Yamaguchi et al. | 378/19 |

Primary Examiner—Janice A. Howell
Assistant Examiner—T. N. Grigsby
Attorney, Agent, or Firm—Arnold B. Silverman

[57] ABSTRACT

Radiography apparatus includes radiation sources for substantially simultaneously generating first and second radiation beams. Collimators are interposed between the radiation source and an object to be exposed to radiation in order to convert the first and second radiation beams into parallel fan-shaped beams. Radiation detectors convert the radiation passing through the object being examined into an electrical signal containing image information. The radiation detector may have at least one scintillator to convert radiation which is passed through an object into light and at least one self-scanning array of photodiodes to convert the light into an electrical signal containing image information. Fiber optic coupling may be provided between the scintillator and the self-scanning array of photodiodes. Means for effecting subtraction of image information resulting from the first beam from image information resulting from the second beam will serve to permit elimination of obstructions to effective visualization of portions of the objects desired to be visualized such as, for example, coronary arteries in a human being. Apparatus may be provided for receiving the signal to store, process or display the image as by a visual display system. The method of effecting such radiographic imaging including subtraction of undesirable portions of the image information.

22 Claims, 4 Drawing Figures

RADIOGRAPHY APPARATUS AND METHOD

BACKGROUND OF THE INVENTION

1. Field of the Invention

This invention relates to radiography apparatus and an associated method and, more specifically, it relates to an efficient system for noninvasively visualizing moving portions of an object by employing substantially parallel beams of radiation and subtraction techniques.

2. Description of the Prior Art

The advantageous use of radiation, such as x-rays, gamma rays and nuclear particles has long been known in medical, industrial and other environments. A wide variety of systems and procedures have been employed in such uses depending, in part, upon safety considerations, the nature of the object to be imaged and equipment limitations. See generally U.S. Pat. Nos. 3,767,931; 3,829,701; 3,866,047; 3,934,151; 3,947,689 and 3,973,127.

It has also been known to use various forms of photodetectors, such as photomultipliers, in such systems. See generally U.S. Pat. Nos. 4,010,371 and 4,029,964. It has also been known to employ self-scanning photodiode arrays for spectroscopy (Snow, Research-Development, April 1976) and for medical and nonmedical uses (See our U.S. Pat. No. 4,179,100, the disclosure of which is hereby expressly incorporated herein by reference).

It has also been known to provide systems wherein collimated radiation is permitted to pass through an object and impinge upon a scintillator screen with fiber optic coupling means transporting the light to one or more arrays of self-scanning photodiodes which emit a responsive electrical signal which may then be computer enhanced or otherwise processed or imaged See U.S. Pat. No. 4,179,100.

In spite of these prior disclosures, there is needed an effective means for low dosage, clear visualization of coronary arteries and other portions of the body as well as other objects with high resolution, while eliminating undesired obstruction to full visualization, particularly with respect to moving sections which are desired to be visualized.

SUMMARY OF THE INVENTION

The apparatus and associated method of the present invention have provided an effective means for noninvasively visualizing moving portions of an object to be investigated.

In general, the invention contemplates radiation source means establishing first and second radiation beams which pass through collimator beams to establish first and second substantially parallel radiation beams. These parallel beams are passed through the object and the radiation passing through the object is received by radiation detector means disposed on the opposite side of the object. The radiation detector means convert the radiation into responsive electrical signals which contain image information. This image information is delivered to signal receiving means which are operatively associated with the radiation detector means to store, process or display the image information.

In instances where it is desired to visualize coronary arteries of a human or animal, for example, the use of the two parallel beams permits subtraction to be effected. This can be particularly useful, for example, where it is desired to visualize human or animal coronary arteries. The subtraction permits elimination from an obstructing position of ribs, blood vessels of the lung (which may impede visualization due to contrast material which has been introduced into the vessels) and other items which would otherwise obstruct full visualization of the coronary artery. Also, the use of the parallel beams permits the artery to be visualized in two positions.

It is an object of the present invention to provide improved radiography means which are adapted to provide a clear picture of objects while minimizing interference from portions of the object which are not desired to be visualized.

It is another object of the present invention to provide such a system which permits visualization of portions of human and animal bodies noninvasively merely through introduction of contrast media intravenously.

It is a further object of this invention to provide such apparatus and associated method which minimizes the influence of scattered radiation and will provide sharp images even at low contrast.

It is a further object of the invention to provide such a system which permits the use of reduced radiation dosage while providing images of desired clarity.

It is a further object of the invention to provide such a radiography system which offers high contrast sensitivity and high spatial resolution.

It is yet another object of the present invention to provide such a system which will permit effective visualization of moving portions of the object being studied.

It is a further object of the invention to provide such a system which permits identification and visualization of fine arteries of the heart.

These and other objects of the invention will be more fully understood from the following description of the invention on reference to the illustrations appended hereto.

DESCRIPTION OF THE PREFERRED EMBODIMENTS

As used herein, the term "object" or words of similar import will refer to various types of objects through which it is desired to pass radiation for test or diagnostic or other purposes including, but not limited to, humans and animals, specimens removed from humans and animals, non-destructive testing and security purposes. While for purposes of clarity of description, specific reference will be made herein to a preferred use in medical environments, it will be appreciated that other forms of objects may be employed in connection with the apparatus of this invention in addition to medical uses and such other uses are expressly contemplated.

As used herein, the terms "self-scanning array of photodiodes", "self-scanning integrated array of photodiodes" and words of similar import shall mean one or more integrated circuit elements having a plurality of photodiodes, each associated with a storage capacitor on which it integrates electrical charges and a multiplex switch for periodic readout by means of an integrated switch register scanning circuit. This term shall expressly include, but not be limited to, linear arrays having about 60 to 4096 (preferably about 256 to 4096) photodiodes per integrated circuit and the associated circuitry, as well as planar or rectangular arrays of photodiodes. These arrays may have about 70 photodiodes per linear millimeter of array, for example.

As used herein, the term "image information" shall refer to the electrical signals emerging from the photodiode array, images or data created by use of said electrical signals, with or without intervening storage or modification thereof and images created with or without addition to or subtraction from the image data.

Figure 1:
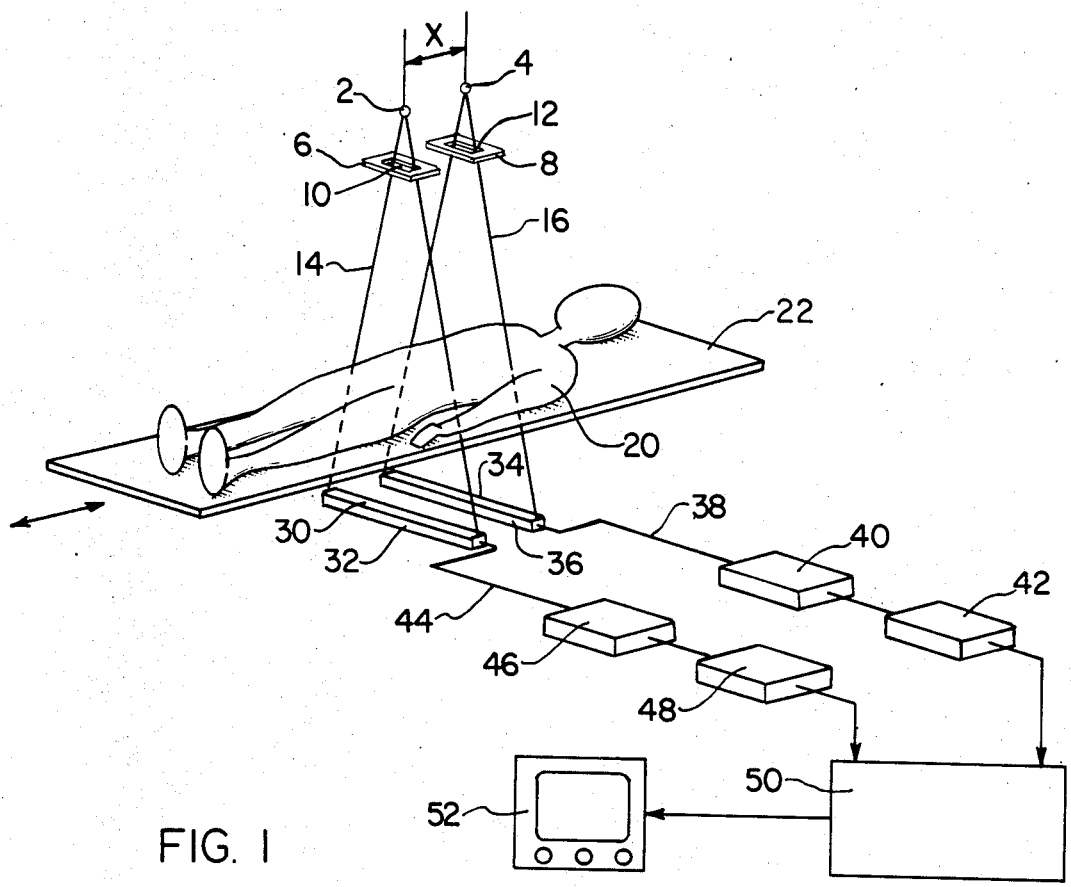
FIG. 1 is a schematic illustration of a form of radiography system of the present invention.

Referring now more specifically to FIG. 1, there is shown schematically a system of the present invention. A pair of radiation source means 2,4 are spaced from each other a distance X. This distance is preferably about 1 to 2 inches, measured center to center. Collimator means, which in the form shown are a pair of collimators 6,8 each having an elongated slot 10,12, serves to convert the generally cone shaped radiation beam, such as an x-ray beam emitted by the radiation source means into a pair of generally parallel fan-shaped beams 14, 16. The object 20 to be studied, in the form shown, is a human patient which is supported by a table 22. It is contemplated, in the form shown that the table will be moved in the directions indicated by the arrows with the radiation source means 2,4, collimators 6,8 and the detector system to be described hereinafter being stationary. It is noted also that the distance X is generally aligned with the direction of travel of the patient 20.

Associated with each beam 14,16 and adapted to receive the portion of the beam, which passes through the object 20 are means for converting penetrating radiation to electrical signals. In the form illustrated these take the form of a pair of scintillator means 30,34 which are optically coupled as by fiber optic means (not shown) to underlying detectors 32,36. The scintillator means 30,34, which may each be a relatively narrow phosphor screen, converts the x-ray or other radiation energy into visible light photons. For certain systems, for example, in cases where low KVP is employed and silicon or germanium diodes are used with low intensity radiation, the radiation may be allowed to impinge directly on the diodes without the use of separate scintillator means or optical coupling means. Also, the scintillator means may contact the detectors directly without the use of optical couplings.

Optical coupling means such as fiber optic means may serve to deliver light emitted by the scintillator means to the detectors. The detectors 32,36, which preferably are arrays of self-scanning photodiodes disposed in linear array form, emit responsive electrical signals which correspond to the light which impinges thereon. The electrical signals contain image information. The electrical signals emerging from detectors 32 are carried by wire 44 through amplifier 46 which amplifies the signal and then through analog-to-digital converter 48 which converts the signal into digital form. The digitized signal is then delivered to computer means 50. Similarly, detector 36 emits electrical signals over wire 38 through amplifier 40 and analog-to-digital converter 42 to digital memory means 50, such as a computer.

The output of the computer may be visually displayed on cathode ray tube or TV screen 52.

The computer which, in the form shown is a digital computer, receives the electrical signals in the memory bank and then, with or without modification thereof, presents the desired image in desired output form such as by presenting a visual image, a stored image or a computer printout of the data.

In a preferred form of the present invention, it is contemplated that by controlling the distance X between the radiation source means 2,4 and the relative speed of travel of the table and object 20 with respect to the apparatus or vice versa in the direction indicated, the interval of time between when one fan-shaped beam 14 passes through the object and the next fan-shaped beam 16 passes through the object may be controlled so as to permit effective subtraction of components not desired in the final image information. More specifically, for example, the time interval between the two beams passing through the identical section of the object may be on the order of about 50 to 150 milliseconds. This time period is substantially less than the time period for a human heart cycle, which is on the order of about 500 milliseconds. As a result, the present system permits taking two images within the same heart cycle. If it is desired to visualize the coronary arteries noninvasively, the individual may be injected through a vein with a suitable contrast agent such as iodine which may be delivered in quantities of about 8 to 15 cc per second for a period of about 4 seconds. Within the computer, elements which are not desired to be visualized and which are not moving except for the relative translational movement of the object 20 with respect to the apparatus may be emphasized through subtraction techniques. First image information is subtracted from second image information to form final image information. The information about the portions of the object which are stationary, except for relative movement with respect to the fan shaped beams, is nullified. For example, the individual's ribs and blood vessels of the lung may be removed from the image through subtraction. As the coronary arteries are moving, the resultant image information will contain and permit visualization of two distinct positions of the coronary artery with great clarity. The two images will have one image dark and the other light separated by the distance the artery has moved during the time interval which has elapsed between the taking of the two subtracted images. This permits quantitative measurement of both the degree of narrowing of the vessel and displacement of the same. This approach further permits one to freeze the motion of the coronary artery in order to achieve the benefit of short line-by-line exposure and to use the linear fan-shaped geometry to achieve a maximum degree of rejection of scattered radiation.

Figure 2:
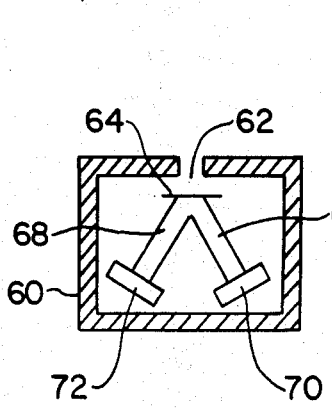
FIG. 2 is a cross-sectional illustration of a modified form of self-scanning array of photodiodes and associated coupler means.
Figure 3:
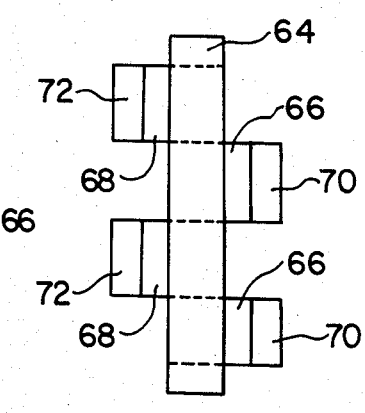
FIG. 3 is a top plan view of a portion of the photodiode array of FIG. 2.

Referring to FIGS. 2 and 3, a preferred form of self-scanning photodiode array for use in the present invention will be considered. In this embodiment an enclosure 60 which is radiation opaque is provided with an opening 62 into which the fan-shaped beam of radiation which has passed through the object 20 may pass. The scintillator 64 is in contact with a generally V-shaped fiber optic coupler which has a first series of legs 66 extending to one side and a second series of legs 68 extending to the other side. Associated with the fiber optic legs 66 are a series of self-scanning photodiode arrays 70. Associated with the fiber optic legs 68 are a series of self-scanning photodiode arrays 72. The arrays 70,72 are disposed substantially perpendicular to the fiber optic fibers. In operation, the x-ray will impinge upon the unitary scintillator strip 64 and will by the fiber optic means 66,68, be delivered to the staggered arrays of self-scanning photodiodes 70,72 with which the respective legs are associated. As is shown in FIG. 3, in this embodiment the self-scanning photodiode arrays 70,72 are positioned in staggered fashion and are optically coupled to scintillator means 64 to provide continuous receipt of light emerging from the scintillator means by the arrays 70,72. Alternate light pipes provide light to alternate photodiode arrays from alternate sections of the scintillator means 64. This embodiment provides unique means for minimizing the risk of undesired gaps in image information as displayed visually.

As an alternate to the preferred approach shown in FIGS. 2 and 3, precisely dimensioned self-scanning photodiode arrays may be placed in a linear, close abutting relationship with direct fiber optic coupling so as to resist undesired gaps.

As a further alternate the scintillator means may be secured directly to the detector means without use of independent optic coupling means.

Figure 4:
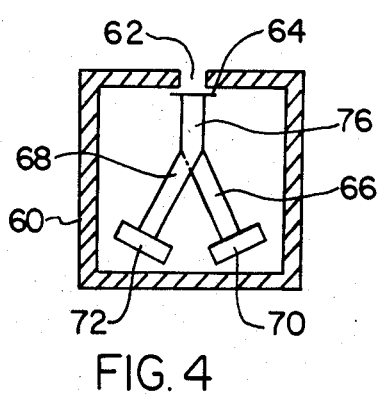
FIG. 4 is a cross-sectional illustration of a modified form of the staggered self-scanning array of photodiodes of FIGS. 2 and 3.

FIG. 4 illustrates a modified form of staggered array which is generally similar to FIGS. 2 and 3 except that a series of alternating individual bent fiber optic couplers 76–68 and 76′ (not shown) –66 deliver the light from the scintillator means 64, respectively, to photodiode arrays 70,72.

A method of the present invention involves providing sources of two radiation beams, an object to be imaged and radiation detectors. The radiation beams are generally parallel and are caused to impinge on the object in different paths with portions thereof passing through the object. Radiation detectors convert the portions of the radiation beams passing through the object into electrical signals containing first image information from the first beam and second image information from the second beam. The image information of the two beams is subtracted by means known to those skilled in the art so as to permit reduction or elimination of portions which are not desired to appear in the final visualized object.

It will be appreciated that while primary emphasis has been placed herein upon visualization of moving parts of an object with further emphasis upon the human body, the invention is not so limited. While the invention is particularly advantageous for use in visualizing moving portions of the human body such as coronary arteries, arteries of the kidney and other internal portions, it will be appreciated that the apparatus and method are equally adapted for use with animals and inanimate objects. A further advantage of the invention is the fact that the detectors are not in the path of the radiation beam and, therefore, damage to the detectors due to radiation is resisted and "noise" is minimized.

While for purposes of illustration, collimators with a single slit have been emphasized herein, it will be appreciated that if desired more than one slit in a given collimator or a single collimator having a slit for each beam may be provided if desired While specific reference has been made to a radiation source providing x-rays or gamma rays, the invention is not so limited and other forms of radiation such as particulate radiation including protons and mesons, for example, may be employed. In connection with the particulate radiation as well as other forms, a generally rectangular beam having parallel sides may be used in lieu of a fan beam.

While, for simplicity of disclosure, reference has been made herein to the preferred use of self-scanning arrays of photodiodes as the preferred means of detecting radiation passing through the object being tested, it will be appreciated that the invention is not so limited. For example, other forms of solidstate diode arrays may be used. A general reference herein to "radiation detectors" shall be deemed to encompass these types of detectors as well as other means of converting radiation into responsive electrical signals. With respect to diode arrays, single linear arrays, multiple linear arrays, staggered arrays, arrays disposed generally in a single plane ("planar arrays") or other suitable patterns may be employed.

While for purposes of simplicity of description herein, in general, examples showing a vertically oriented radiation beam path have been employed, it will be appreciated that radiation may be directed from any desired angle or angles and also that the patient or object may be oriented or moved vertically or angularly with respect to the floor of the room. Also, the patient may remain stationary and the radiation source means and detector system may be subjected to relative movement with respect to the patient.

A further advantage of the present invention in connection with human objects is that the use of venous contrast material in the present invention reduces the risk of adverse side effect which may be encountered in inter-arterial injections necessary for film imaging techniques.

It will be appreciated that the two radiation beams may be separate tubes or both beams may be generated from a single anode, e.g. a dual anode x-ray tube.

Whereas particular embodiments of the invention have been described above for purposes of illustration, it will be evident to those skilled in the art that numerous variations of the details may be made without departing from the invention as defined in the appended claims.

We claim:

1. A method of radiographic imaging of an object having a beating heart comprising establishing a first planar fan beam of penetrating radation and a second planar fan beam of penetrating radiation substantially parallel to said first beam, said first beam and said second beam both impinging on said object and being spaced apart along a given line substantially perpendicular to the planes of the beams, establishing relative movement between said object and both of said first and second beams in a direction substantially parallel to said given line and at a speed such the time interval between the two beams poassing through the identical section of the object is substantially less than the time period for said beating heart, converting the portion of said first beam which passes through said object into a first electrical signal, converting the portion of said second beam which passes through said object into a second electrical signal, processing said first and second electrical signals to obtain first image information and second image information respectively, subtracting said first image information from said second image information to form final image information such that information about portions of the object which are stationary, except for said relative movement, is nullified and displaying said final image information.

2. The radiographic method of claim 1, comprising using scintillator means, fiber optic means and at least one self-scanning array of photodiodes for converting said first and second beams of penetrating radiation into first and second electrical signals respectively.

3. The method of radiographic imaging of claim 2 including said first planar fan beam and said second planar fan beam being spaced apart about one to two inches from each other.

4. The method of radiographic imaging of claim 2, said object being a human being.

5. The method of radiographic imaging of claim 4 including quantitatively measuring both the degree of narrowing and the displacement of the coronary artery of said human being.

6. The method of radiographic imaging of claim 5 including introducing contrast material into a vein of said human being prior to establishing said relative movement.

7. Radiography apparatus, for imaging of an object having a beating heart, comprising means for establishing a first planar fan beam of penetrating radiation and a second planar fan beam of penetrating radiation substantially parallel to said first beam, said first beam and said second beam being spaced apart along a given line substantially perpendicular to the planes of the beams, means for positioning said object within a given region of space such that said object will be impinged upon by both of said first and said second planar beams, means for establishing relative movement between said given region of space and both of said first and said second planar beams in a direction substantially parallel to said given line and at a speed such that the time interval between the two beams passing through the identical section of said given region of space is substantially less than the time period of said beating heart, means for converting the portion of said first beam which passes through said given region of space into a first electrical signal, means for converting the portion of said second beam which passes through said given region of space into a second electrical signal, means for processing said first and said second electrical signals to obtain first image information and second image information respectively, means for subtracting said first image information from said second image information to form final image information such that information about portions of said object which are stationary, except for said relative movement, is nullified and means for displaying said fianl image information.

8. The radiography apparatus of claim 7 further comprising digital computer means for enhancing portions of said final image information.

9. The radiography apparatus of claim 7, said first planar fan beam and said second planar fan beam being spaced apart by about one to two inches.

10. The radiography apparatus of claim 7, said means for processing first and said second electrical signals to obtain said first image information and said second image information comprises amplifier means, analog-to-digital converter means and digital memory means.

11. The radiography apparatus of claim 10 wherein said digital memory means includes a digital computer.

12. The radiography apparatus of claim 10, said first and second planar fan beams being established substantially simultaneously.

13. The radiography apparatus of claim 7 wherein said means for converting the portion of said first beam which passes through said given region of space into a first electrical signal and said means for converting the portion of said second beam which passes through said given region of space into a second electrical signal each include scintillator means and an array of solid-state detector means,
 said scintillator means adapted to convert said radiation into light,
 fiber optic coupling means for delivering light from said scintillator means to said solid-state detector means, and
 said array of solid-state detector means adapted to receive said light and emit responsive electrical signals.

14. The radiography apparatus of claim 13 including
 said fiber optic coupling means being so associated with said scintillator means and said solid-state detector means as to deliver light emitted by said scintillator means with substantial continuity to the said arrays of solid-state detector means.

15. The radiography apparatus of claim 14 wherein each said array of solid-state detector means includes at least one self-scanning photodiode array.

16. The radiography apparatus of claim 15, said means for establishing said first and second planar fan beams of penetrating radiation further comprising first and second collimator means.

17. The radiography apparatus of claim 16 including each said scintillator means having at least one phosphor screen.

18. The radiography apparatus of claim 17 including each self-scanning array of photodiodes being a planar array having two rows of linear self-scanning phototiode arrays disposed with said linear arrays of a first said row being staggered with respect to said linear arrays of a second said row, and
 said fiber optic coupling means connecting alternate portions of said scintillator means with a photodiode array from said first row and a photodiode array from said second row, whereby adjacent portions of said scintillator means will be optically coupled to photodiode arrays in different rows.

19. The radiography apparatus of claim 18 including said photodiode arrays of one said row being so positioned with respect to said photodiode arrays of the other said row that at least one transverse edge of an array of one said row will be substantially aligned with a transverse edge of an array of said other row, whereby appreciable gaps and overlaps will be substantially completely eliminated and substantially continuous image information will be created.

20. The radiography apparatus of claim 19 including a radiation opaque housing surrounding said scintillator means, optical coupling means and self-scanning photodiode arrays, and
 said housing having an opening generally aligned with said scintillator means.

21. The radiography apparatus of claim 20 including each said self-scanning array of photodiodes including a linear array of about 60 to 4096 photodiodes per integrated circuit.

22. The radiography apparatus of claim 21 including each said self-scanning array of photodiodes having more than one linear array of self-scanning photodiodes and said arrays being oriented generally parallel with respect to each other.

* * * * *

UNITED STATES PATENT AND TRADEMARK OFFICE
CERTIFICATE OF CORRECTION

PATENT NO. : 4,692,937

DATED : September 8, 1987

INVENTOR(S) : DONALD SASHIN and ERNEST J. STERNGLASS

It is certified that error appears in the above-identified patent and that said Letters Patent is hereby corrected as shown below:

Column 3, line 36, delete comma after "beam".

Claim 1, column 6, line 51, after "such" --that-- should be inserted.

Claim 7, column 7, line 46, "fianl" should be --final--.

Claim 10, column 7, line 54, --said-- should be inserted after "processing".

Claim 18, column 8, lines 32-33, "phototiode" should be --photodiode--.

Signed and Sealed this

Seventeenth Day of May, 1988

Attest:

DONALD J. QUIGG

*Attesting Officer*

*Commissioner of Patents and Trademarks*